United States Patent
Adams et al.

(10) Patent No.: US 6,403,574 B1
(45) Date of Patent: Jun. 11, 2002

(54) AZETIDINECARBOXAMIDE DERIVATIVES FOR TREATING CNS DISORDERS

(75) Inventors: David Reginald Adams; Corinna Dagmar Bodkin; Ian Anthony Cliffe; Howard Langham Mansell; Nathaniel Julius Monck, all of Wokingham; Robin Gerald Shepherd, deceased, late of Berkshire, all of (GB), by Joy Miriam Shepherd, legal representative

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/600,628

(22) PCT Filed: Jan. 22, 1999

(86) PCT No.: PCT/GB99/00219

§ 371 (c)(1),
(2), (4) Date: Sep. 17, 2001

(87) PCT Pub. No.: WO99/37612

PCT Pub. Date: Jul. 29, 1999

(30) Foreign Application Priority Data

Jan. 23, 1998 (GB) .............................................. 9801500
Nov. 6, 1998 (GB) .............................................. 9824457

(51) Int. Cl.⁷ ........................ A61K 31/397; A61P 25/00; C07D 205/04

(52) U.S. Cl. .................................. 514/210.17; 548/952
(58) Field of Search ....................... 548/952; 514/210.17

(56) References Cited

U.S. PATENT DOCUMENTS 4,226,861 A   10/1980   Cale, Jr. ...................... 424/244

FOREIGN PATENT DOCUMENTS

| EP | 0 102 194 | 3/1984 |
| EP | 0 102 740 | 3/1984 |
| EP | 0 194 112 | 9/1986 |
| GB | 872447 | 7/1961 |

Primary Examiner—Robert W. Ramsuer
Assistant Examiner—Rebecca Anderson
(74) Attorney, Agent, or Firm—Foley & Lardner

(57) ABSTRACT

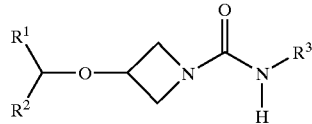

A compound of formula (1), wherein: $R^1$ is aryl; $R^2$ is H, alkyl or aryl; and $R^3$ is hydrogen or alkyl; pharmaceutically acceptable addition compounds thereof; and the use of the compounds in therapy, particularly for the treatment and prophylaxis of CNS disorders such as anxiety and epilepsy.

27 Claims, No Drawings

AZETIDINECARBOXAMIDE DERIVATIVES FOR TREATING CNS DISORDERS

This is a 371 of international application PCT/GB99/00219 with international filing date Jan. 22, 1999 published in English.

The present invention relates to chemical compounds useful in the treatment of disorders of the central nervous system (CNS), such as anxiety and all forms of epilepsy, particularly in humans. The invention also relates to the use of such compounds, pharmaceutical preparations containing such compounds and to methods of preparing such compounds.

Anxiety disorders affect an estimated 73 million people world-wide. The benzodiazepines have provided the dominant therapy for anxiety over the past three decades and there is no doubt that they are remarkably effective anxiolytics. However, chronic administration of benzodiazepines produces severe dependence liability, withdrawal syndromes, and side effects (sedation, amnesia, muscle relaxation). The only non-benzodiazepine anxiolytic that has been launched over the past decade is the 5-HT receptor ligand buspirone (Buspar®). This drug has had a remarkable commercial success despite being regarded as a weak anxiolytic (compared with the benzodiazepines) and having a long latency to onset of therapeutic action (2–4 weeks). In addition, buspirone and all related 5-HT$_{1A}$ partial agonists suffer from a dose-limiting side-effect profile comprising nausea, vertigo and endocrine changes.

The aetiology of anxiety disorders is not fully understood, but it is now established that benzodiazepines act by potentiating GABAergic neurotransmission although there is strong evidence that other neurotransmitter systems are modulated indirectly—in particular, the serotonergic and noradrenergic systems. Many pharmaceutical companies have invested considerable resource into the development of serotonergic anxiolytics. However, it is now apparent that ligands selective for 5-HT receptor subtypes, despite displaying anxiolytic-like activity in a restricted range of anxiety models, have, at best, very weak and/or non-dose-related anxiolytic effects in the clinic. The 5-HT$_3$ receptor antagonists are now discredited as psychotropics: they have a restricted range of activity in functional and anxiety models; they show no convincing anxiolytic effects in the clinic; and they are now accepted only as useful antiemetics. The 5-HT$_{2A}$ antagonists similarly are regarded as ineffective in terms of psychotropic activity. The clinical utility of 5-HT$_{1A}$ receptor agonists and partial agonists is severely limited by their intrinsically weak action and by the dose-limiting side-effects (vertigo, endocrine changes, nausea) which become more intense as the agonist efficacy of these molecules is increased. The selective CCK$_B$ receptor antagonists have displayed an unimpressive preclinical profile similar to that of selective 5-HT ligands such as the 5-HT$_3$ antagonists.

Serotonergic anxiolytics include the selective serotonin reuptake inhibitors (SSRIs) which, in addition to displaying antidepressant properties, are also effective in anxiety disorders such as panic disorder and obsessive-compulsive disorder. However, as with their antidepressant action, the major drawback with these compounds is the long delay (6–8 weeks) in the onset of clinical improvement following chronic administration.

A strategy in recent years towards improving the clinical profile of classical benzodiazepines is that of developing benzodiazepine receptor partial agonists, according to the rationale that they would have a more selective anxiolytic action and be less liable to induce dependence. However, this approach appears to have failed owing to the very weak anxiolytic actions of these compounds and their poor side-effect profiles (there is either a low or non-existent ratio between anxiolytic and sedative doses).

U.S. Pat. No. 4,956,359 and EP-A-0194112 disclose 3-aryloxy and 3-arylthio azetidinecarboxamides and their anti-convulsant and anti-epileptic activity. These compounds, like the benzodiazepines, have low water solubility which leads to difficulties in formulation. The presence of an oxygen or sulphur atom, present as a linking atom between the aryl group and the azetidine ring, is a key feature of these compounds since such atoms can affect molecular conformation as well as increasing electron density in the aryl rings.

There remains therefore a need for novel anxiolytic and anti-epileptic agents which do not suffer the above-mentioned drawbacks.

It has now been surprisingly found that inserting a methylene-containing group between the aryl group and the oxygen atom, and thereby increasing conformational freedom and decreasing election density in the aryl ring, is not detrimental to pharmacological effect. Further, insertion of the methylene-containing group gives a surprising improvement in the binding affinity to the GABA$_A$ receptor.

According to the present invention there is provided a chemical compound of formula (1)

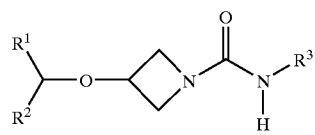

(1)

wherein:
R$^1$ is aryl;
R$^2$ is H, alkyl or aryl; and
R$^3$ is hydrogen or alkyl;
and pharmaceutically acceptable addition compounds thereof.

Reference in the present specification to an "alkyl" group means a branched or unbranched, cyclic or acyclic, saturated or unsaturated (e.g. alkenyl or alkynyl) hydrocarbyl radical. Where cyclic or acyclic the alkyl group is preferably C$_1$ to C$_{12}$, more preferably C$_1$ to C$_8$ (such as methyl, ethyl, propyl, isopropyl butyl, isobutyl, tert-butyl, amyl, isoamyl, hexyl, heptyl, octyl).

Reference in the present specification to an "aryl" group means a mono or bicyclic aromatic group, such as phenyl or naphthyl.

The alkyl and aryl groups may be substituted or unsubstituted. Where substituted, there will generally be 1 to 3 substituents present, preferably 1 or 2 substituents. Substituents may include:
 carbon containing groups such as
  alkyl
  aryl, arylalkyl (e.g. substituted and unsubstituted phenyl, substituted and unsubstituted benzyl);
 halogen atoms and halogen containing groups such as haloalkyl (e.g. trifluoromethyl);
 oxygen containing groups such as
  alcohols (e.g. hydroxy, hydroxyalkyl, (aryl)(hydroxy)alkyl),
  ethers (e.g. alkoxy, alkoxyalkyl, aryloxyalkyl),
  aldehydes (e.g. carboxaldehyde), ketones (e.g. alkylcarbonyl, alkylcarbonylalkyl, arylcarbonyl, arylalkylcarbonyl, arylcarbonylalkyl), 
acids (e.g. carboxy, carboxyalkyl), 
acid derivatives such as esters 
    (e.g. alkoxycarbonyl, alkoxycarbonylalkyl, alkycarbonylyoxy, alkycarbonylyoxyalkyl) and amides 
    (e.g. aminocarbonyl, mono- or dialkyl-aminocarbonyl, aminocarbonylalkyl, mono- or dialkylaminocarbonylalkyl, arylaminocarbonyl); 
nitrogen containing groups such as 
    amines (e.g. amino, mono- or dialkylamino, aminoalkyl, mono- or dialkylaminoalkyl), 
    azides, 
    nitriles (e.g. cyano, cyanoalkyl), 
    nitro; 
sulphur containing groups such as 
    thiols, thioethers, sulphoxides and sulphones 
        (e.g. alkylthio, alkylsulfinyl, alkylsufonyl, alkylthioalkyl, alkylsulfinylalkyl, 
alkylsulfonylalkyl, arylthio, arylsulfinyl, arylsulfonyl, arylthioalkyl, arylsulfinylalkyl, arylsulfonylalkyl); 
and heterocyclic groups containing one or more, preferably one, heteroatom, 
    (e.g. thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl).

Preferred substituents include alkyl, aryl, nitrile, halo, or a halogen-containing group such as trifluoromethyl.

As used herein, the term "alkoxy" means alkyl-O— and "alkoyl" means alkyl-CO—.

As used herein, the term "halogen" means a fluorine, chlorine, bromine or iodine radical, preferably a fluorine or chlorine radical.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its pure form.

In the compounds of formula (1), preferably $R^1$ is a substituted or unsubstituted aryl group selected from phenyl and naphthyl, more preferably $R^1$ is a substituted phenyl or naphthyl, more preferably $R^1$ is a phenyl or naphthyl having 1 to 3 substituents and most preferably $R^1$ is a phenyl or naphthyl having 1 or 2 substituents. In a preferred embodiment of the invention, $R^1$ is a mono- or di-substituted phenyl group, preferably a mono-substituted phenyl group.

Where $R^1$ is a naphthyl group, $R^1$ is preferably a 2-naphthyl group.

Where $R^1$ is a phenyl having 1 substituent, the phenyl group is preferably para- or meta-substituted. Where $R^1$ is a phenyl having 2 substituents, the phenyl group is preferably 2,4-disubstituted, 2,5-disubstituted, 3,4-disubstituted or 3,5 disubstituted, and more preferably 3,4-disubstituted.

The preferred substituent groups are selected from halo (preferably fluoro and chloro), trifluoromethyl, tertiary-butyl, phenyl and CN.

Where $R^1$ is disubstituted, it is preferred that $R^1$ is substituted by two halo groups, the same or different, preferably the same, or by two trifluoromethyl groups.

The most preferred $R^1$ groups are selected from 3-chlorophenyl, 3-fluorophenyl, 4-chlorophenyl, 4-fluorophenyl, 3-trifluoromethylphenyl, 4-trifluoromethylphenyl, 3,4-dichlorophenyl and 3,4-difluorophenyl.

In the compound of formula (1), preferably $R^2$ is H, $C_{1-4}$ alkyl or mono-substituted phenyl. Where $R^2$ is $C_{1-4}$ alkyl, it is preferred that $R^2$ is acyclic hydrocarbyl, preferably methyl or ethyl. Where $R^2$ is mono-substituted phenyl, it is preferred that $R^2$ is a halo-substituted phenyl, preferably substituted in the para-position.

In one embodiment of the present invention, $R^3$ is alkyl, preferably $C_{1-4}$ alkyl, and more preferably alkenyl, alkynyl, hydroxyalkyl, alkoxyalkyl or unsubstituted saturated cyclic or acyclic hydrocarbyl.

In a further embodiment of the present invention, $R^3$ is selected from H and $C_{1-4}$ alkyl, preferably from H, alkenyl, alkynyl, hydroxyalkyl, alkoxyalkyl and unsubstituted saturated cyclic and acyclic hydrocarbyl, and more preferably from H, propyl, 2-propenyl, 2-propynyl and 2-hydroxypropyl.

Particularly preferred compounds are as follows:

| $R^1$ | $R^2$ | $R^3$ |
|---|---|---|
| 4-Cl—$C_6H_4$ | H | 2-propenyl |
| 3,4-$Cl_2$—$C_6H_3$ | H | 2-propenyl |
| 3,4-$F_2$—$C_6H_3$ | H | 2-propenyl |
| 3-$CF_3$—$C_6H_4$ | H | 2-propenyl |
| 4-$CF_3$—$C_6H_4$ | H | 2-propenyl |
| 4-F—$C_6H_4$ | H | 2-propenyl |
| 4-F—$C_6H_4$ | H | 2-propynyl |
| 4-Cl—$C_6H_4$ | H | 2-propynyl |
| 4-Cl—$C_6H_4$ | 4-Cl—$C_6H_4$ | 2-propenyl |
| 4-Cl—$C_6H_4$ | 4-Cl—$C_6H_4$ | 2-hydroxypropyl |
| 3-$CF_3$—$C_6H_4$ | H | H |
| 3-$CF_3$—$C_6H_4$ | methyl | H |

Of these, the preferred compounds are 3-(3,4-Dichlorobenzyloxy)-N-(2-propenyl)azetidine-1-carboxamide, 3-(3-(Trifluoromethyl)benzyloxy)-N-(2-propenyl)azetidine-1-carboxamide, 3-(4-(Trifluoromethyl)benzyloxy)-N-(2-propenyl)azetidine-1-carboxamide, 3-(4-Fluorobenzyloxy)-N-(2-propenyl)azetidine-1-carboxamide, 3-(Bis(4-chlorophenyl)methoxy)-N-(2-propenyl)azetidine-1-carboxamide, (R)-3-(Bis(4-chlorophenyl)methoxy)-N-(2-hydroxypropyl)azetidine-1-carboxamide, 3-(1-(3-Trifluoromethylphenyl)ethyloxy)-azetidine-1-carboxamide, and 3-(3-(Trifluoromethyl)benzyloxy)-azetidine-1-carboxamide.

According to a further aspect of the present invention there is provided a compound according to the present invention for use in therapy.

The compounds of the present invention may be used in the treatment (including prophylaxis) of CNS disorders. In particular, the compounds of the present invention may be used in the treatment (including prophylaxis) of anxiety, epilepsy, insomnia, including travel insomnia and insomnia associated with terminal illness, alcohol withdrawal syndrome, chronic and acute pain, neurodegenerative diseases (for example, senile dementia) and symptoms related to withdrawal from substance abuse. The compounds may also be used in the relief of spasticity. The compounds of the present invention may also be used in muscle relaxation prior to surgery or surgical manipulation or as pre-medication prior to surgery. In a preferred embodiment of the present invention, the compounds are used in the treatment (including prophylaxis) of anxiety or epilepsy.

Anxiety includes generalised anxiety disorder (GAD), panic disorder, panic disorder plus agoraphobia, simple (specific) phobias (e.g. arachnophobia, performance anxiety such as public speaking), social phobias, post-traumatic stress disorder, anxiety associated with depression, and obsessive compulsive disorder (OCD).

Epilepsy is a chronic disorder characterised by recurrent seizures. Two forms of epilepsy exist—partial and generalised epilepsy—and each type is subdivided into idiopathic (cause unknown) or symptomatic (cause known). There are two fundamental types of seizures: partial seizures which includes simple partial seizures, complex partial seizures, and partial seizures secondarily generalised; and generalised seizures which includes generalised tonic-clonic seizures (grand mal), absence seizures (petit mal), myoclonic seizures, atonic seizures, clonic seizures, and tonic seizures.

According to a further aspect of the present invention there is provided use of a compound of the present invention in the manufacture of a medicament for the treatment (including prophylaxis) of CNS disorders, preferably anxiety, epilepsy, insomnia, including travel insomnia and insomnia associated with terminal illness, alcohol withdrawal syndrome, chronic and acute pain, neurodegenerative diseases, symptoms relating to withdrawal from substance abuse or spasticity, and more preferably anxiety or epilepsy.

According to a further aspect of the present invention there is provided use of a compound of the present invention in the manufacture of a medicament for muscle relaxation prior to surgery or surgical manipulation or as pre-medication prior to surgery.

The invention further provides a method of treatment (including prophylaxis) of CNS disorders, preferably anxiety, epilepsy, insomnia, including travel insomnia and insomnia associated with terminal illness, alcohol withdrawal syndrome, chronic and acute pain, neurodegenerative diseases, symptoms relating to withdrawal from substance abuse and spasticity, and more preferably anxiety or epilepsy, comprising administering to a patient in need of such treatment an effective dose of a compound according to the present invention.

The invention further provides a method of muscle relaxation prior to surgery or surgical manipulation or a method of pre-medication prior to surgery, comprising administering to a patient in need thereof an effective dose of a compound according to the present invention.

According to a further aspect of the present invention there is provided a method of preparing a compound of the present invention.

Compounds of the present invention may be prepared according to the reaction scheme (where P is a nitrogen protecting group). $R^1$, $R^2$, and $R^3$ are as previously defined. The ether (IV) may be formed by reaction of the azetidinol (II) either with an arylalkanol (III, X=OH) and diethylazo dicarboxylate and triphenyl phosphine or with an arylalkyl chloride, bromide, iodide, mesylate or tosylate (III, X=Cl, Br,I, mesylate, tosylate) and a strong base such as sodium hydride. Formation of the azetidine (V) may be achieved by reaction of (IV) with a suitable nitrogen deprotection agent. For example, if P is a diphenylmethyl group, then deprotection may be carried out by treatment with 1-chloroethyl chloroformate followed by methanol. The urea (I) is formed by reaction of azetidine (V) with an N-alkylisocyanate or an N-alkylcarbamoyl chloride and a base such as triethylamine or potassium carbonate. Alternatively, the urea may be prepared directly from the azetidine (IV) without isolation of an intermediate such as the secondary amine (V). For example, when P is a diphenylmethyl group, azetidine (IV) may be treated with phosgene followed by amine $R^3NH_2$ to give urea (I) directly.

Reaction Scheme

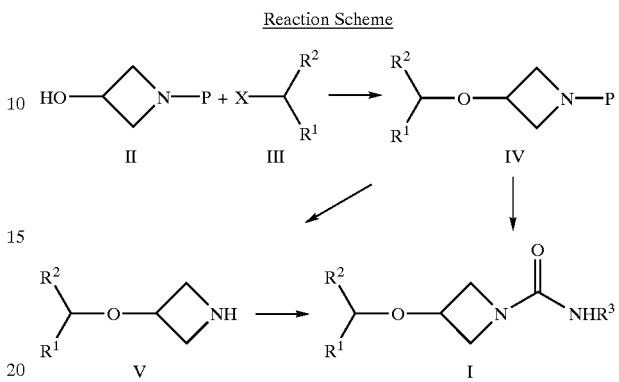

The invention further provides a pharmaceutical composition comprising a compound according to the present invention in combination with a pharmaceutically acceptable carrier or excipient and a method of making such a composition comprising combining a compound according to the present invention with a pharmaceutically acceptable carrier or excipient.

Compounds of the present invention may be administered in a form suitable for oral use, for example a tablet, capsule, aqueous or oily solution, suspension or emulsion; for topical use including transmucosal and transdermal use, for example a cream, ointment, gel, aqueous or oil solution or suspension, salve, patch or plaster; for nasal use, for a example a snuff, nasal spray or nasal drops; for vaginal or rectal use, for example a suppository; for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oil solution or suspension. In general the above compositions may be prepared in a conventional manner using conventional excipients, using standard techniques well known to those skilled in the art of pharmacy. Preferably, the compound is administered orally.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

It will be appreciated that the dosage levels used may vary over quite a wide range depending upon the compound used, the severity of the symptoms exhibited by the patient and the patient's body weight.

The invention will now be described in detail with reference to the following examples. It will be appreciated that the invention is described by way of example only and modification of detail may be made without departing from the scope of the invention.

EXPERIMENTAL

Measurement of Binding Affinity to the $GABA_A$ Receptor with [$^{35}$S]-TBPS

The ability of test compounds to bind to the $GABA_A$ receptor was measured in membranes prepared from rat fore-brain using the procedure described by Green et al (Green, A. R., Misra, A., Murray, T. K., Snape, M. F. & Cross, A. J. Neurophamacology, 1996, 35, 1243–1250).

Binding assays were performed in plastic microtitre plates. In each study total assay volume contained [$^{35}$S]-TBPS (1 nM final concentration), membrane preparation and displacing drugs where appropriate. Drug solutions were prepared at a concentration of 10 mM in an appropriate solvent (EtOH, DMSO or $H_2O$) and then diluted with assay buffer. Non-specific binding was determined using GABA. The free ligand concentration was determined by counting aliquots of the [$^{35}$S]-TBPS solution. The concentration of test compounds required to displace 50% of the specific binding ($IC_{50}$) was determined from displacement curves. The test results are shown in Table 1

TABLE 1

Binding Affinities to the $GABA_A$ receptor

| Example number | $IC_{50}$ ($\mu$M) |
| --- | --- |
| 2 | 56 |
| 3 | 87 |
| 4 | 91 |
| 6 | 64 |
| 7 | 32 |

Antagonism of 3-MPA-Induced Seizures

Several animal seizure models are available for the screening and characterisation of anticonvulsant (antiepileptic) drugs. Most models employ a chemical convulsant to induce seizures and the anticonvulsant potencies of novel compounds are measured in terms of their ability to increase the dose of convulsant required to induce a seizure response (or to prolong the latency to seizure onset following a bolus dose of the convulsant). Most chemical convulsants work by blocking the neurotransmitter function of gamma-aminobutyric acid (GABA), the predominant inhibitory neurotransmitter in the mammalian brain. This can be achieved by blocking the postsynaptic action of GABA using pentylenetetrazol or bicuculline, or via a presynaptic action using a GABA synthesis inhibitor to decrease GABA release into the synapse. In this case, the inhibitor of glutamate decarboxylase (GAD), 3-mercaptopropionic acid (3-MPA), was used as the convulsant challenge agent. Anticonvulsant effects of test compounds were determined by their abilities to significantly increase the dose of 3-MPA required to initiate a seizure response.

Male albino T/O strain mice (obtained from Tuck) weighing 28–40 g were used in these studies. Animals were assigned randomly to treatment groups and vehicle or test drug (at a dose of 30 mg/kg) were administered p.o. to groups of 12 animals 60 min before the administration of a bolus dose of 3-MPA intravenously. Immediately following 3-MPA administration, each mouse was placed individually into a cage for observation. The seizure response of each animal was scored quantally as present or absent (response or non-response) during the 5 min period immediately following 3-MPA administration. A seizure response was defined as the onset of the initial clonic phase of the seizure (abrupt loss of righting reflex accompanied by vocalisation). The seizure threshold (in terms of mg/kg i.v. of 3-MPA required to evoke a seizure response) was determined in each treatment group by a sequential up/down method followed by modified probit analysis of the quantal data. A range of doses of 3-MPA was prepared (12.5–200.0 mg/kg i.v.) increasing by a constant geometric factor ($^3\sqrt{2}$), which was found in pilot studies to generate suitable data for analysis by this method.

In these studies, 3-MPA was obtained from Sigma.

Test compounds were prepared as solutions dissolved in 45% w/v aqueous 2-hydroxypropyl-β-cyclodextrin. 3-MPA was dissolved in isotonic saline and its pH adjusted to 6 using 1M sodium hydroxide solution. Drugs were administered in a dose volume of 10 ml/kg body weight. The test results are shown in Table 2.

TABLE 2

Antagonism of 3-MPA-Induced Seizures: Results of Testing

| Compound | SC | SV |
| --- | --- | --- |
| Example 1 | 35.98 | 15.7 |
| Example 2 | 66.7 | 16.2 |
| Example 3 | 129.3 | 15.6 |
| Example 4 | 75.7 | 16.2 |
| Example 5 | 42.8 | 15.6 |

SC=seizure threshold after treatment with test drug
SV=seizure threshold in vehicle treated group Measurement of Anxiolytic Activity in Mice Using the Elevated Zero-maze Model The elevated "zero-maze" is a modification of the elevated plus-maze model of anxiety which incorporates both traditional and novel ethological measures in the analysis of drug effects (Shepherd, J. K., Grewal, S. S., Fletcher, A., Bill, D. J. and Dourish, C. T., Behavioural and pharmacological characterisation of the elevated "zero-maze" as an animal model of anxiety. *Psychopharmacology*, 1994, 116, 56–64).

Male Sprague-Dawley rats (Charles River) weighing 300–450 gm are used. Animals are group-housed (5 per cage; cage size: 40×40×20 cm) in a temperature-controlled environment (20±2° C.), under a 12h light-dark cycle (lights on: 08:00 hours). Food and water are made freely available. Four hours prior to testing, animals are transferred to clean cages and moved to the testing room in order to habituate to the testing environment.

The maze is comprised of a black Perspex annular platform (105 cm diameter, 10 cm width) elevated to 65 cm above ground level, divided equally into four quadrants. Two opposite quadrants are enclosed by clear red Perspex walls (27 cm high) on both the inner and outer edges of the platform, while the remaining two opposite quadrants are surrounded only by a Perspex "lip" (1 cm high) which serves as a tactile guide to animals on these open areas. To facilitate the measurement of locomotor activity, the apparatus is divided into octants by splitting each quadrant into equal halves using high contrast white lines. The apparatus is illuminated by dim red lighting arranged in such a manner as to provide similar lux levels in both the open and closed quadrants (40–60 lux). A video camera, connected to a VCR in an adjacent observation room, is mounted overhead in order to record behaviour on the maze for subsequent analysis.

Chlordiazepoxide hydrochloride [CDP; Sigma Chemical Co. Ltd. Poole], which has previously been shown to display robust anxiolytic-like effects in the zero-maze, serves as positive control. Drugs are typically dissolved in a 45% solution of 2-hydroxypropyl-β-cyclodextrin, and administered orally by gavage 1 hour prior to zero-maze testing.

Rats are placed on a closed quadrant and a 5 min test period is recorded on video-tape. The maze is cleaned with a 5% methanol/water solution and dried thoroughly between test sessions. Five behavioural parameters are scored: [1] percentage of time spent on the open areas; [2] frequency of head dips over the edge of the platform when subjects are located in either the open or the end of the closed quadrants; [3] frequency of stretch-attend postures (SAP) from closed to open quadrants, determined when the subject, on a closed quadrant, exhibits an elongated body posture stretched forward with at least the snout passing over the open/close divide; [4] frequency of rearing; and [5] the number of line crossings. Animals are scored as being in the open area when all four paws were in an open quadrant, and in the closed area only when all four paws passed over the open/closed divide. All testing is carried out between 1100 and 1700 hours.

An increase in the frequency of head dips is considered to be a measure of anxiolytic activity. The compound of example 1 was found to be effective at a dose of 30 mg/Kg.

CHEMISTRY

Preparation of 1-(Diphenylmethyl)-3-azetidinol

This compound was prepared according to the method of Anderson and Lok (*J. Org. Chem.*, 1972, 37, 3953, the disclosure of which is incorporated herein by reference), m.p. 111–112° C. (lit. m.p. 113° C.).

Preparation of 3-(4-Chlorobenzyloxy)-1-(diphenylmethyl) azetidine (1)

A solution of 1-diphenylmethyl-3-azetidinol (25 mmol) in DMF (100 mL) was added at 0° C. to a suspension of NaH (60% disp.in oil, 30 mmol) in DMF (50 mL). The reaction mixture was stirred at room temperature for 1 h, then 4-chlorobenzylchloride (25 mmol) was added dropwise at 0° C. and the reaction mixture stirred at room temperature for 3 h. The reaction was quenched with water and extracted with ethyl acetate (3×50 mL), the extracts were washed with water and brine, dried ($MgSO_4$) and concentrated in vacuo. The residue was purified by chromatography [$SiO_2$; hexane-ethyl acetate (9:1)] to yield the product as a yellow oil (7.3 g, 80%). The material was used in the next step without further purification.

Example 1

3-(4-Chlorobenzyloxy)-N-(2-propenyl)azetidine-1-carboxamide (2)

Phosgene solution (1.75-M in toluene, 24 mmol) was added at 0° C. to a solution of compound (1) (20 mmol) in $CH_2Cl_2$ (40 mL). The reaction mixture was stirred at room temperature for 90 min, concentrated in vacuo, then redissolved in $CH_2Cl_2$ (40 mL) and treated with allylamine (42 mmol) at 0° C. The reaction was stirred for 4 h at room temperature, then water (40 mL) was added and the layers were separated. The aqueous layer was extracted with further $CH_2Cl_2$ (2×40 mL). The organic layers were washed with dilute HCl (20 mmol) and brine, dried ($MgSO_4$) and concentrated in vacuo. The residue was triturated using diethyl ether to give the product (2) as a crystalline solid (3.5 g, 60%), m.p. 110–111° C. Found: C, 59.84; H, 6.11; N, 9.98. $C_{14}H_{17}ClN_2O_2$ requires: C, 59.89; H, 9.6.10; N, 9.97%.

Preparation of 3-(3,4-Dichlorobenzyloxy)-1-(diphenylmethyl)azetidine (3)

This material was prepared from 1-diphenylmethyl-3-azetidinol (6.0 g) and alpha,3,4-trichlorotoluene using the procedure described for compound (1) (yield 92%).

Example 2

3-(3,4-Dichlorobenzyloxy)-N-(2-propenyl)azetidine-1-carboxamide (4)

This material was prepared from compound (3) (9.2 g) using the procedure described for compound (2) (yield 75%), m.p. 88–89° C. Found: C, 53.43; H, 5.18; N, 8.85, $C_{14}H_{16}Cl_2N_2O_2$ requires C, 53.35; H, 5.12; N, 8.88%.

Preparation of 3-(3-(Trifluoromethyl)benzyloxy)-1-(diphenylmethyl)azetidine (5)

This material was prepared from 1-diphenylmethyl-3-azetidinol (5 g) and alpha'-bromo-alpha,alpha,alpha-trifluoro-m-xylene using the procedure described for compound (1) (yield 91%).

Example 3

3-(3-(Trifluoromethyl)benzyloxy)-N-(2-propenyl)azetidine-1-carboxamide (6)

This material was prepared from compound (5) (7.5 g) using the procedure described for compound (1) (yield 64%), m.p. 108° C. Found: C, 57.29; H, 5.44; N, 8.87, $C_{15}H_{17}F_3N_2O_2$ requires C, 57.32; H, 5.45; N, 8.91%.

Preparation of 3-(4-(Trifluoromethyl)benzyloxy)-1-(diphenylmethyl)azetidine (7)

This material was prepared from 1-diphenylmethyl-3-azetidinol (6.0 g) and α'-bromo-α,α,α-trifluoro-p-xylene using the procedure described for compound (1) (yield 77%).

Example 4

3-(4-(Trifluoromethyl)benzyloxy)-N-(2-propenyl)azetidine-1-carboxamide (8)

This material was prepared from compound (7) (7.7 g) using the procedure described for compound (2) (yield 72%), m.p. 120° C. Found: C, 57.27; H, 5.45; N, 8.86. $C_{15}H_{17}F_3N_2O_2$ requires C, 57.32; H, 5.45, N, 8.91%.

Preparation of 3-(4-Fluorobenzyloxy)-1-(diphenylmethyl)azetidine (9)

This material was prepared from 1-diphenylmethyl-3-azetidinol (6.0 g) and 4-fluorobenzyl bromide using the procedure described for compound (1) (yield 83%).

Example 5

3-(4-Fluorobenzyloxy)-N-(2-propenyl)azetidine-1-carboxamide (10)

This material was prepared from compound (9) using the procedure described for compound (2), m.p. 97–99° C. Found: C, 63.57; H, 6.59; N, 10.66. $C_{14}H_{17}ClN_2O_2$ requires C, 63.62; H, 6.48; N, 10.59.

Preparation of 3-(Bis-(4-chlorophenyl)methoxy-1-diphenylmethyl)azetidine (11)

A solution of 4,4'-dichlorobenzhydrol (25 mmol),p-toluenesulfonic acid (18.4 mmol) and 1-(diphenylmethyl)-3-azetidinol (8.4 mmol) in benzene (100 mL) was heated under reflux in a Dean-Stark apparatus for 3 h. The solution was cooled, washed with sodium hydrogen carbonate (saturated aqueous solution, 100 mL), dried ($MgSO_4$) and concentrated in vacuo. The residue was purified by chromatography [$SiO_2$; hexane-diethyl ether (5:1)] to yield the product (11) as a thick oil that crystallized on standing (2.4 g, 62%).

Example 6

3-(Bis(4-chlorophenyl)methoxy)-N-(2-propenyl)azetidine-1-carboxamide (12)

This material was prepared from compound (11) using the procedure described for compound (2) (yield 17%) as a crystalline solid. Found: C, 56.38; H, 5.10; N, 6.51. $C_{20}H_{20}Cl_2N_2O_2.2H_2O$ requires: C, 56.21; H, 5.66; N, 6.56%.

Example 7

Preparation of (R)-3-(Bis(4-chlorophenyl)methoxy)-N-(2-hydroxypropyl)azetidine-1-carboxamide (13)

This material was prepared from compound (11) and (R)-(−)-1-amino-2-propanol using the procedure described for compound (2) (yield 57%) as a crystalline solid. Found: C, 58.74; H, 5.42; N, 6.84. $C_{20}H_{22}Cl_2N_2O_3$ requires: C, 58.69; H, 5.42; N, 6.84%.

Example 8

3-(3-Trifluoromethyl)benzyloxy-N-azetidine-1-carboxamide (14)

To a solution of 3-(3-trifluoromethyl)benzyloxy-1-(diphenylmethyl)azetidine (5) (5.3 mmol) in dichloromethane (15 mL) at 0° C., was added a solution of phosgene (1.75M in toluene, 6.4 mmol). The reaction mixture was stirred at room temperature for 2 h, concentrated in vacuo, then redissolved in THF (15 mL) and treated with ammonium hydroxide (5 mL), added in one portion, at 0° C. The reaction was stirred vigorously for 15 h at room temperature, then water (50 mL) and ethyl acetate (40 mL) were added and the layers were separated. The aqueous layer was extracted with ethyl acetate (2×40 mL), dried ($MgSO_4$) and concentrated in vacuo. The residue was triturated using ethyl acetate (10 mL) to yield (14) as a solid (0.91 g, 63%), mp. 167° C. (ethyl acetate). Found: C, 52.44; H, 4.72; N, 10.23. $C_{14}H_{17}ClN_2O_2$ requires: C, 52.56; H, 4.78; N, 10.21.

Preparation of 3-(1-(3-Trifluoromethylphenyl)ethyloxy)-1-(diphenylmethyl)azetidine (15)

To a solution of α-methyl-3-trifluoromethylbenzyl alcohol (53 mmol), diisopropylethyl amine (105 mmol) in dichloromethane (150 mL) under nitrogen and cooled to 0° C., was added methane sulfonyl chloride (63.1 mmol) dropwise over 10 min. The reaction was stirred for 15 h. Water (200 mL) was added and the resulting mixture stirred for 10 min, poured into potassium carbonate (10% wt/wt aqueous solution, 200 mL) and extracted with dichloromethane (3×150 mL). Combined organic extracts were washed with brine (50 mL) once and then dried ($Na_2SO_4$), filtered and concentrated in vacuo. The residue was dissolved in ethyl ether and washed through a pad of silica, eluting with more ether. The filtrate was concentrated in vacuo. This material was used directly, as shown below.

A solution of 1-diphenylmethyl-3-azetidinol (42 mmol) in dimethyl formamide (20 mL) was added via pipette, to a suspension of NaH (60% disp.in oil, 50 mmol) in dimethyl formamide (80 mL) at 0° C. The reaction mixture was stirred at room temperature for 15 min, the crude material from above (assumed 53 mmol) was added dropwise as a solution in dimethyl formamide (30 mL) at 0° C. and the reaction mixture stirred at room temperature for 2 h. The reaction was poured into water (200 mL) and extracted with ethyl acetate (3×50 mL), the extracts were washed with water (200 mL) and brine (50 mL), dried ($MgSO_4$) and concentrated in vacuo. The residue was purified by chromatography ($SiO_2$; hexane/ethyl acetate 9/1) to yield 3-(1-(3-trifluoromethylphenyl)ethyloxy)-1-(diphenylmethyl) azetidine (15) as a yellow oil (11.2 g, yield 65%). The material was used in the next step without further purification.

Example 9

3-(1-(3-Trifluoromethylphenyl)ethyloxy)-azetidine-1-carboxamide (16)

This material was prepared from compound (15) using the procedure described for compound (14) (yield 62%) as a crystalline solid, mp. 130.5–131.5° C. (diisopropyl ether). Found: C, 54.24; H, 5.26; N, 9.69. $C_{14}H_{17}ClN_2O_2$ requires: C, 54.17; H, 5.24.; N, 9.71.

Examples 10 to 43 see Table 3.

The products were prepared using the procedure described for compound (2).

TABLE 3

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 10 | 17 | 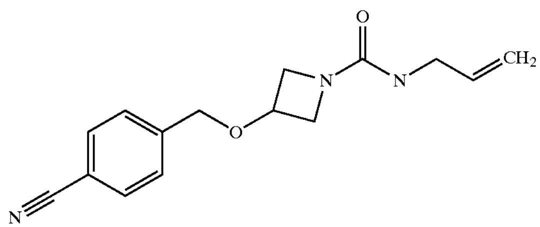 | C15H17N3O2 | 271.32 | 95–96 | 66.69 | 6.29 | 15.32 | 66.40 | 6.32 | 15.48 | |
| 11 | 18 | 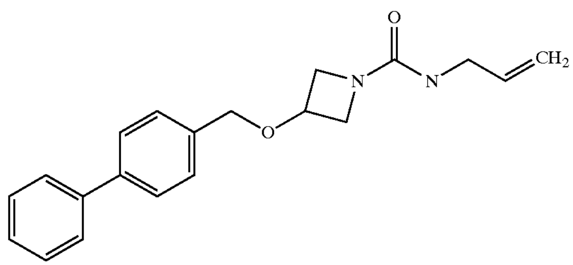 | C20H22N2O2 | 322.41 | 160.0 | 74.52 | 6.87 | 8.61 | 74.51 | 6.88 | 8.68 | |
| 12 | 19 | 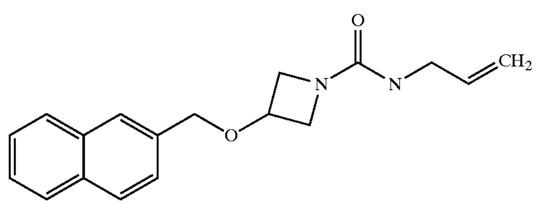 | C18H20N2O2 | 296.37 | 141–142 | 72.96 | 6.77 | 9.65 | 72.95 | 6.80 | 9.45 | |
| 13 | 20 | 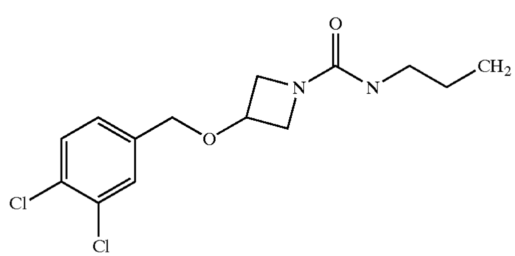 | C14H18Cl2N2O2 | 317.22 | 89–90 | 53.00 | 5.74 | 8.73 | 53.01 | 5.72 | 8.83 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 14 | 21 | 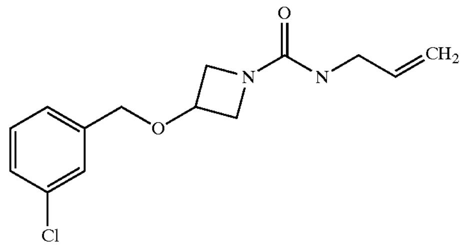 | C14H17ClN2O2 | 280.76 | 67–68 | 59.94 | 6.12 | 9.95 | 59.89 | 6.10 | 9.97 | |
| 15 | 22 | 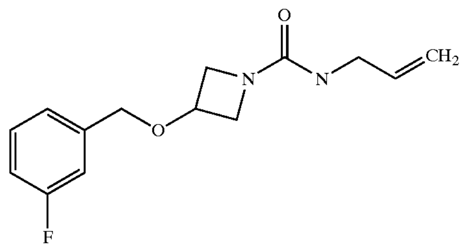 | C14H17FN2O2 | 264.30 | 59–60 | 63.55 | 6.55 | 10.59 | 63.62 | 6.48 | 10.59 | |
| 16 | 23 | 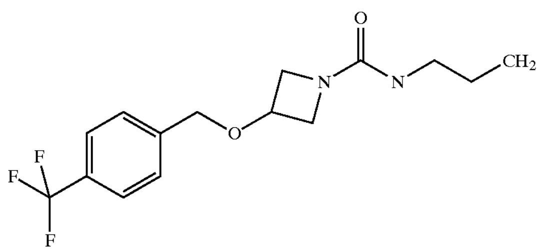 | C15H19F3N2O2 | 316.33 | 128–129 | 56.92 | 6.09 | 8.83 | 56.96 | 6.05 | 8.85 | |
| 17 | 24 | 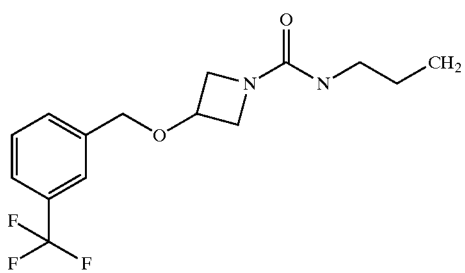 | C15H19F3N2O2 | 316.33 | 62–63 | 56.89 | 6.21 | 8.82 | 56.96 | 6.05 | 8.85 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 18 | 25 | Chiral | C15H19F3N2O3 | 332.33 | 67–68 | 54.25 | 5.81 | 8.42 | 54.21 | 5.76 | 8.43 | |
| 19 | 26 | Chiral | C15H19F3N2O3 | 332.33 | 67–68 | 54.21 | 5.87 | 8.41 | 54.21 | 5.76 | 8.43 | |
| 20 | 27 | Chiral | C15H19F3N2O3 | 332.33 | 97–98 | 54.09 | 5.76 | 8.39 | 54.21 | 5.76 | 8.43 | |
| 21 | 28 | Chiral | C15H19F3N2O3 | 332.33 | 97–98 | 54.39 | 5.82 | 8.44 | 54.21 | 5.76 | 8.43 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 22 | 29 | Chiral | C14H18Cl2N2O3 | 333.22 | 88–89 | 50.46 | 5.34 | 8.39 | 50.46 | 5.44 | 8.40 | |
| 23 | 30 | Chiral | C14H18Cl2N2O3 | 333.22 | 88–89 | 50.49 | 5.36 | 8.61 | 50.46 | 5.44 | 8.40 | |
| 24 | 31 | Chiral | C14H19ClN2O3 | 298.77 | 85–86 | 56.27 | 6.40 | 9.35 | 56.28 | 6.41 | 9.37 | |
| 25 | 32 | 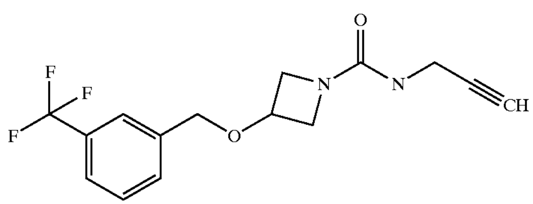 | C15H15F3N2O2 | 312.29 | 90–91 | 57.73 | 4.94 | 8.91 | 57.69 | 4.84 | 8.97 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 26 | 33 | 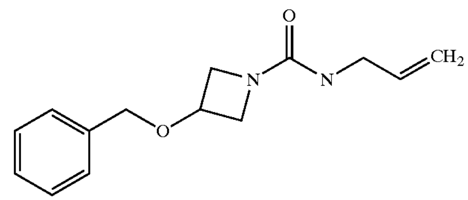 | C14H18N2O2 | 246.31 | 76–77 | 68.29 | 7.35 | 11.37 | 68.27 | 7.37 | 11.37 | |
| 27 | 34 | Chiral | C14H19FN2O3 | 282.32 | 73–74 | 59.49 | 6.87 | 9.93 | 59.56 | 6.78 | 9.92 | |
| 28 | 35 | 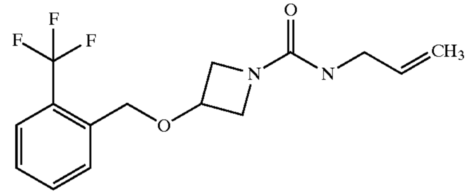 | C1H17F3N2O2 | 314.31 | 63.0 | 57.34 | 5.47 | 8.92 | 57.32 | 5.45 | 8.91 | |
| 29 | 36 | 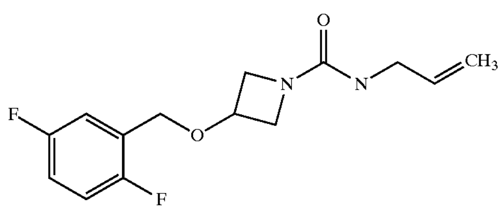 | C14H16F2N2O2 | 282.29 | 75.0 | 59.59 | 5.72 | 9.88 | 59.57 | 5.71 | 9.92 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 30 | 37 | 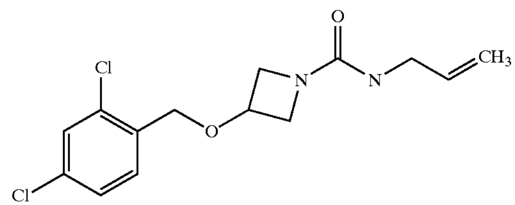 | C14H16Cl2N2O2 | 315.20 | 100.0 | 53.15 | 4.99 | 8.86 | 53.35 | 5.12 | 8.88 | |
| 31 | 38 | 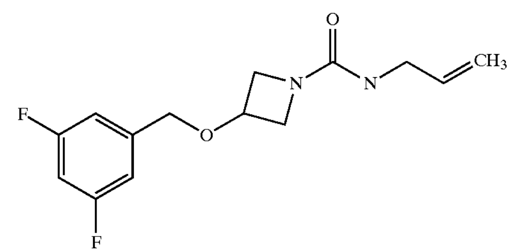 | C14H16F2N2O2 | 282.29 | 79.0 | 59.55 | 5.73 | 9.90 | 59.57 | 5.71 | 9.92 | |
| 32 | 39 | 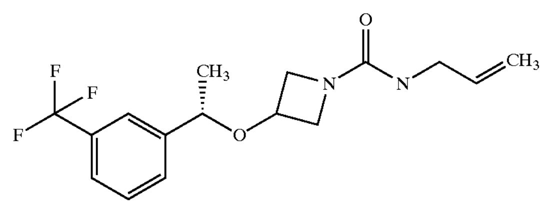 | C16H19F3N2O2 | 328.34 | oil | | | | | | | a |
| 33 | 40 | 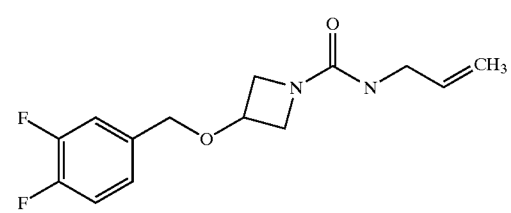 | C14H16F2N2O2 | 282.29 | 82.5–85 | 59.72 | 5.69 | 9.98 | 59.57 | 5.71 | 9.92 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 34 | 41 | 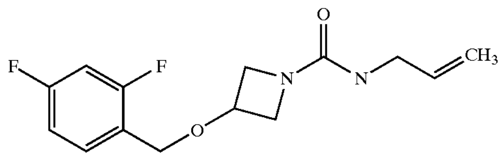 | C14H16F2N2O2 | 282.29 | 91–92.5 | 59.58 | 5.62 | 9.94 | 59.51 | 5.71 | 9.92 | |
| 35 | 42 | 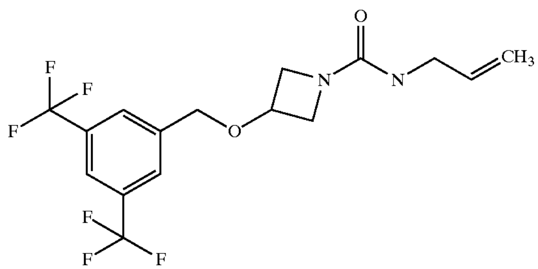 | C16H16F6N2O2 | 382.31 | 80.5–81.5 | 50.38 | 4.25 | 7.32 | 50.27 | 4.22 | 7.32 | |
| 36 | 43 | Chiral | C14H19ClN2O3 | 298.77 | 76–78 | 56.94 | 6.34 | 10.25 | 56.28 | 6.41 | 9.37 | |
| 37 | 44 | 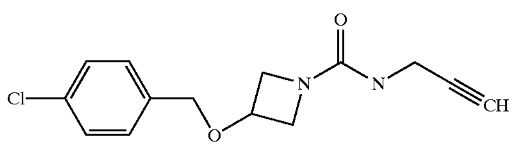 | C14H15ClN2O2 | 278.74 | 123–124 | 60.88 | 5.58 | 9.91 | 60.33 | 5.42 | 10.05 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 38 | 45 | 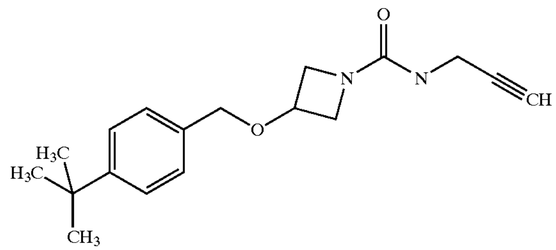 | C18H24N2O2 | 300.40 | 94–96 | 71.89 | 8.08 | 9.28 | 71.97 | 8.05 | 9.32 | |
| 39 | 46 | Chiral | C18H28N2O3 | 320.44 | oil | | | | | | | b |
| 40 | 47 | Chiral | C14H19FN2O3 | 282.32 | 72–73 | 59.32 | 6.84 | 9.81 | 59.56 | 6.78 | 9.92 | |
| 41 | 48 | 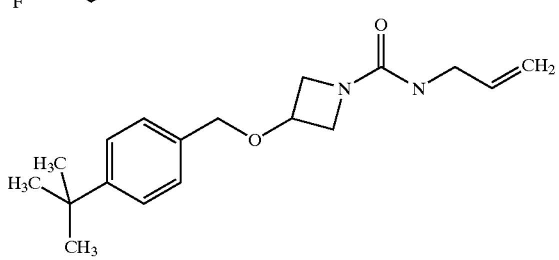 | C18H26N2O2 | 302.42 | 79–80 | 71.25 | 8.79 | 9.36 | 71.49 | 8.67 | 9.26 | |

TABLE 3-continued

| Exampleno | Compound No. | Structure | Formula | MWt | mp | Cfound | Hfound | Nfound | Cexp | Hexp | Nexp | Note |
|---|---|---|---|---|---|---|---|---|---|---|---|---|
| 42 | 49 | 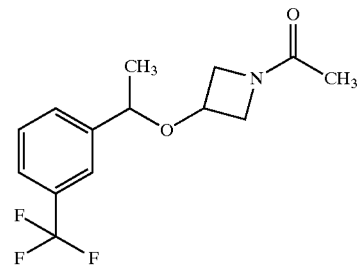 | C14H17F3N2O2 | 302.30 | 110.5–112 | 55.64 | 5.77 | 9.26 | 55.63 | 5.67 | 9.26 | |
| 43 | 50 | 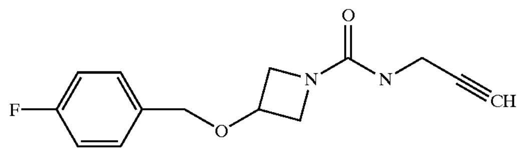 | C14H15FN2O2 | 262.29 | 94–96 | 64.29 | 5.47 | 10.70 | 64.11 | 5.76 | 10.68 | |

Footnotes for Table 3:
Footnote a: IR: 3296, 2980, 2943, 2877, 1638, 1545, 1400, 1377, 1330, 1203, 1166, 1127, 1073, 706 cm$^{-1}$.
Footnote b: IR: 3319, 2963, 2872, 1634, 1549, 1469, 1403, 1327, 1269, 1184, 1130, 1083, 818 cm$^{-1}$.

What is claimed is:

1. A compound of formula (1)

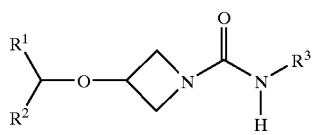

wherein: $R^1$ is substituted or unsubstituted aryl; $R_2$ is hydrogen, substituted or unsubstituted alkyl, substituted or unsubstituted alkenyl, substituted or unsubstituted alkynyl, substituted or unsubstituted cyclic alkyl, substituted or unsubstituted cyclic alkenyl, or substituted or unsubstituted aryl; and $R^3$ is hydrogen, substituted or unsubstituted alkyl, substituted or unsubstituted alkenyl, substituted or unsubstituted alkynyl, substituted or unsubstituted cyclic alkyl, or substituted or unsubstituted cyclic alkenyl.
and pharmaceutically acceptable addition compounds thereof.

2. A compound according to claim 1 wherein $R^1$ is a substituted or unsubstituted aryl group selected from phenyl and naphthyl.

3. A compound according to claim 1 wherein $R^1$ has 1, 2 or 3 substituent groups.

4. A compound according to claim 1, wherein $R^1$ is substituted with one or more substituent groups selected from halo, trifluoromethyl, tertiary-butyl, CN and phenyl.

5. A compound according to claim 4 wherein said halo group is fluoro or chloro.

6. A compound according to claim 1 wherein $R^1$ has 1 substituent and is a meta- or para-substituted phenyl group.

7. A compound according to claim 1 wherein $R^1$ is 3-chlorophenyl, 4-chlorophenyl, 3-fluorophenyl, 4-fluorophenyl, 3-(trifluoromethyl)phenyl, 4-(trifluoromethyl)phenyl, 3,4-dichlorophenyl or 3,4-difluorophenyl.

8. A compound according to claim 1 wherein $R^1$ is selected from a 2,4-disubstituted phenyl, a 2,5-disubstituted phenyl, a 3,4-disubstituted phenyl and a 3,5-disubstituted phenyl.

9. A compound according to claim 1 wherein $R^1$ is substituted by two halo groups, the same or different, or by two trifluoromethyl groups.

10. A compound according to claim 9 wherein $R^1$ is dichloro or difluoro-substituted.

11. A compound according to claim 1 wherein $R^2$ is H.

12. A compound according to claim 1 wherein $R^2$ is $C_{1-4}$ alkyl.

13. A compound according to claim 1 wherein $R^2$ is mono-substituted phenyl.

14. A compound according to claim 1 wherein $R^3$ is alkyl.

15. A compound according to claim 1 wherein $R^3$ is $C_{1-4}$ alkyl.

16. A compound according to claim 1 wherein $R^3$ is alkenyl, alkynyl, hydroxyalkyl or alkoxyalkyl.

17. A compound according to claim 1 wherein $R^3$ is unsubstituted saturated cyclic or acyclic hydrocarbyl.

18. A compound according to claim 1 wherein $R^3$ is selected from propyl, 2-propenyl, 2-propynyl and 2-hydroxypropyl.

19. A compound according to claim 1 wherein $R^3$ is H.

20. A compound according to claim 1 wherein the compound is selected from 3-(4-Chlorobenzyloxy)-N-(2-propenyl) azetidine-1-carboxamide, 3-(3,4-Dichlorobenzyloxy)-N-( 2-propenyl)azetidine-1-carboxamide, 3-(3-(Trifluoromethyl)benzyloxy)-N-(2-propenyl)azetidine-1-carboxamide, 3-(4-(Trifluoromethyl) benzyloxy)-N-(2-propenyl)azetidine-1-carboxamide, 3-(4-Fluorobenzyloxy)-N-(2-propenyl)azetidine-1-carboxamide, 3-(Bis(4-chlorophenyl)methoxy)-N-(2-propenyl)azetidine-1-carboxamide, (R)-3-(Bis(4-chlorophenyl)methoxy)-N-(2-hydroxypropyl)azetidine-1-carboxamide, 3-(1-(3-Trifluoromethylphenyl)ethyloxy)-azetidine-1-carboxamide and 3-(3-(trifluoromethyl)benzyloxy)-azetidine-1-carboxamide.

21. A pharmaceutical composition comprising a compound according to claim 1 in combination with a pharmaceutically acceptable carrier or excipient.

22. A method of treatment of CNS disorders comprising administering to a patient in need of such treatment an effective dose of a compound according to claim 1.

23. A method according to claim 22 wherein said method is for the treatment of anxiety, epilepsy, insomnia, alcohol withdrawal syndrome, chronic and acute pain, neurodegenerative diseases, symptoms relating to withdrawal from substance abuse or spasticity.

24. A method according to claim 22 wherein said method is for the treatment of anxiety or epilepsy.

25. A method of muscle relaxation prior to surgery or surgical manipulation or a method of pre-medication prior to surgery, comprising administering to a patient in need thereof an effective dose of a compound according to claim 1.

26. A method according to claim 23 wherein said insomnia is travel insomnia.

27. A method according to claim 23 wherein said insomnia is insomnia associated with terminal illness.

* * * * *